United States Patent
Reuschling et al.

[11] Patent Number: 5,877,322
[45] Date of Patent: *Mar. 2, 1999

[54] SUBSTITUTED PYRIDINES, THEIR PREPARATION, AND THEIR USE AS PESTICIDES AND FUNGICIDES

[75] Inventors: Dieter Bernd Reuschling, Butzbach; Adolf Heinz Linkies, Frankfurt; Volkmar Wehner, Sandberg; Rainer Preuss, Hofheim; Wolfgang Schaper, Diedorf; Harald Jakobi, Frankfurt; Peter Braun, Nieder-Olm; Werner Knauf, Eppstein; Burkhard Sachse, Kelkheim; Anna Waltersdorfer, Frankfurt; Manfred Kern, Lörzweiler; Peter Lümmen, Niedernhausen; Werner Bonin, Kelkheim, all of Germany

[73] Assignee: Hoechst Schering AgrEvo GmbH, Berlin, Germany

[*] Notice: The term of this patent shall not extend beyond the expiration date of Pat. No. 5,650,417.

[21] Appl. No.: 305,040

[22] Filed: Sep. 12, 1994

[30] Foreign Application Priority Data

Sep. 14, 1993 [DE] Germany ............ 43 31 180.6

[51] Int. Cl.[6] .................................. C07D 213/76
[52] U.S. Cl. .................. 546/297; 546/296; 546/312; 424/405
[58] Field of Search .................. 546/297, 312, 546/296; 424/405

[56] References Cited

U.S. PATENT DOCUMENTS

| | | | |
|---|---|---|---|
| 3,639,413 | 2/1972 | Domenico | 260/294.8 |
| 3,911,183 | 10/1975 | Hinkes | 428/15 |
| 3,965,109 | 6/1976 | Tomlin | 260/294.9 |
| 4,206,215 | 6/1980 | Bailey | 514/332 |
| 4,331,670 | 5/1982 | Nishiyama | 424/263 |
| 4,855,308 | 8/1989 | Kester | 514/332 |

FOREIGN PATENT DOCUMENTS

| | | |
|---|---|---|
| 0182769 | 5/1986 | European Pat. Off. . |
| 182769 | 5/1986 | European Pat. Off. . |
| WO 93/05050 | 3/1993 | WIPO . |

OTHER PUBLICATIONS

Schmid, G.H. et al, Can. J. Chem. 50(8), pp. 1181–1187, May 1972.
March, J. Advanced Organic Chemistry, Wiley Interscience Publication, 1992, pp. 411–413, 613, 654, 780–783.

*Primary Examiner*—Alan L. Rotman
*Assistant Examiner*—Garth M Dahlen
*Attorney, Agent, or Firm*—Frommer Lawrence & Haug LLP

[57] ABSTRACT

The invention relates to compounds of the formula

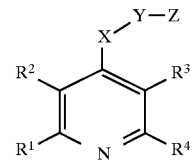

in which $R^1$, $R^2$, $R^3$ and $R^4$ are H, halogen, an aliphatic radical or an aromatic radical, X is O, S or optionally substituted imino, Y is a bond or a bivalent optionally substituted hydrocarbon radical and Z is optionally substituted cycloalkyl or cycloalkenyl. The invention furthermore relates to processes for their preparation and their use as pesticides, in particular as insecticides, acaricides and fungicides.

15 Claims, No Drawings

SUBSTITUTED PYRIDINES, THEIR PREPARATION, AND THEIR USE AS PESTICIDES AND FUNGICIDES

The invention relates to novel substituted 4-amino- and 4-hydroxypyridines, their preparation, and their use as pesticides, in particular as insecticides, acaricides and fungicides.

It has already been disclosed that certain substituted 4-aminopyridines and 4-hydroxypyridines show a fungicidal, acaricidal and insecticidal action (cf. WO 93/05050). However, the biological action of these compounds, in particular at low application rates and concentrations, is not satisfactory in all application ranges.

Novel substituted 4-amino- and 4-hydroxypyridines of the formula 1 have been found, which are biologically active.

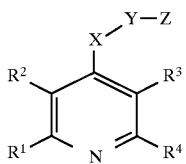
1

The invention therefore relates to compounds of the formula 1 and their salts, in which (1) $R^1$, $R^2$, $R^3$ and $R^4$ are identical or different radicals from the series
$(C_1-C_4)$-alkyl,
$(C_2-C_4)$-alkenyl,
$(C_1-C_4)$-alkoxy
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
R—O—CO—,
halo-$(C_1-C_4)$-alkoxymethyl,
halo-$(C_1-C_4)$-alkoxycarbonyl,
halo-$(C_2-C_4)$-alkenyloxymethyl,
halo-$(C_2-C_4)$-alkenyloxycarbonyl,
$(C_1-C_4)$-alkylthio,
$(C_2-C_4)$-alkenylthio,
$(C_1-C_4)$-alkylsulfinyl,
$(C_2-C_4)$-alkenylsulfinyl
$(C_1-C_4)$-alkylsulfonyl,
$(C_2-C_4)$-alkenylsulfonyl,
aryl,
substituted amino,
cyano,
halogen and
hydrogen;
R is $(C_1-C_{10})$-alkyl,
$(C_2-C_{10})$-alkenyl
$(C_2-C_{10})$-alkynyl,
$(C_3-C_8)$-cycloalkyl or
aralkyl;
aryl is phenyl or
substituted phenyl
aralkyl is aryl-$(C_1-C_4)$-alkyl;

(2) X is O, S, NH or NR, R being defined as above under (1);

(3) Y is a bond or a bivalent hydrocarbon radical having 1 to 6 carbon atoms, in which a methylene group can be replaced by an oxygen atom, and which is optionally substituted by one or more, preferably up to three, identical or different radicals from the series
$(C_1-C_7)$-alkyl
preferably straight-chain $(C_1-C_4)$-alkyl or branched $(C_3-C_7)$-alkyl,
$(C_2-C_4)$-alkenyl,
$(C_3-C_4)$-alkynyl,
halo-$(C_1-C_4)$-alkyl or halogen; and (4) Z is $(C_3-C_8)$-cycloalkyl or $(C_5-C_8)$-cycloalkenyl, which are both optionally substituted by one or more, preferably up to three, identical or different radicals from the series
$(C_1-C_4)$-alkyl
$(C_2-C_4)$ alkenyl,
$(C_1-C_4)$-alkoxy,
$(C_2-C_4)$-alkenyloxy,
$(C_1-C_4)$-alkanoyloxy,
$(C_2-C_4)$-acyl,
$(C_1-C_4)$-alkoxycarbonyl,
$(C_2-C_4)$-alkenyloxycarbonyl,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
halo-$(C_2-C_4)$-acyl,
halo-$(C_1-C_4)$-alkoxycarbonyl,
halo-$(C_2-C_4)$-alkenyloxycarbonyl,
halogen and
hydroxyl
the substituents being cis or trans to Y and the cis-position being preferred and, if only one substituent is present, this, in the case of cyclohexyl, preferably being in the 4-position to Y.

In the above formula 1 "halogen" is to be understood as meaning a fluorine, chlorine, bromine or iodine atom, preferably a fluorine, chlorine or bromine atom;

the expression "$(C_1-C_4)$-alkyl" is to be understood as meaning an unbranched or branched hydrocarbon radical having 1–4 carbon atoms, such as e.g. the methyl, ethyl, propyl, 1-methylethyl, 1-methylpropyl, 2-methylpropyl or 1,1-dimethylethyl radical, the expression "$(C_1-C_{10})$-alkyl" is to be understood as meaning the abovementioned alkyl radicals and also e.g. the pentyl, 2-methylbutyl or the 1,1-dimethylpropyl radical, or the hexyl, heptyl, octyl, 1,1,3,3-tetramethylbutyl, nonyl or decyl radical;

"alkenyl" and "alkynyl" are understood as meaning mono- or polyunsaturated radicals derived from these alkyl radicals;

the expression "$(C_3-C_8)$-cycloalkyl" is preferably understood as meaning the cyclopropyl, cyclobutyl, cyclopentyl, cyclohexyl, cycloheptyl or cyclooctyl group;

the expression "$(C_5-C_8)$-cycloalkenyl" is preferably understood as meaning the cyclopentenyl, cyclohexenyl, cycloheptenyl or cyclooctenyl group;

the expression "$(C_1-C_4)$-alkoxy" is understood as meaning an alkoxy group whose hydrocarbon radical has the meaning indicated under the expression "$(C_1-C_4)$-alkyl";

the expression "$(C_3-C_8)$-cycloalkoxy" is understood as meaning a cycloalkoxy group whose hydrocarbon radical has the meaning indicated under "$(C_3-C_8)$-cycloalkyl";

the expression "$(C_1-C_4)$-alkylthio" is understood as meaning an alkylthio group whose hydrocarbon radical has the meaning indicated under the expression "$(C_1-C_4)$-alkyl" (the same applies for "alkylsulfinyl" and "alkylsulfonyl");

the expression "$(C_1-C_4)$-haloalkyl" is understood as meaning an alkyl group mentioned under the expression "$(C_1-C_4)$-alkyl", in which one or more hydrogen atoms are replaced by the abovementioned halogen atoms, preferably chlorine or fluorine, such as, for example, the trifluoromethyl group, the 2,2,2-trifluoroethyl group, the chloromethyl or fluoromethyl group, the difluoromethyl group or the 1,1,2,2-tetrafluoroethyl group (the same applies for "haloalkenyl");

the expression "$(C_1-C_4)$-haloalkoxy" is understood as meaning a haloalkoxy group whose halohydrocarbon radical has the meaning indicated under the expression "$(C_1-C_4)$-haloalkyl";

"substituted phenyl" is understood as meaning a phenyl radical which carries one or more, preferably up to is three, identical or different substituents from the series halogen, $(C_1-C_4)$-alkyl, halo-$(C_1-C_4)$-alkyl, hydroxy-$(C_1-C_4)$-alkyl, $(C_1-C_4)$-alkoxy, halo-$(C_2-C_4)$-alkoxy, phenoxy, phenyl, nitro, hydroxyl, cyano, $(C_1-C_4)$-alkanoyl, benzoyl, $(C_1-C_4)$-alkanoyloxy, $(C_1-C_4)$-alkoxycarbonyl;

"substituted amino" is understood as meaning an amino group which is substituted by one or two $(C_1-C_4)$-alkyl groups or a $(C_1-C_4)$-alkanoyl group;

a "bivalent hydrocarbon radical having 1 to 6 carbon atoms" is understood as meaning a bivalent radical derived from an n-alkane or n-alkene by removing one hydrogen atom from each of the two terminal carbon atoms of the chain, such as methylene, ethanediyl, trimethylene or tetramethylene;

"$(C_2-C_4)$-acyl" is in particular understood as meaning a $(C_2-C_4)$-alkanoyl radical, such as acetyl, propionyl or butyryl.

The explanation given above applies, specifically if nothing is defined differently, correspondingly for homologous radicals or radicals derived therefrom.

Preferred compounds of the formula 1 and their salts are those in which (1) $R^1$, $R^2$, $R^3$ and $R^4$ are identical or different radicals from the series
$(C_1-C_4)$-alkyl,
$(C_2-C_4)$-alkenyl,
$(C_1-C_4)$-alkoxy
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
R—O—CO—,
halo-$(C_1-C_4)$-alkoxymethyl,
halo-$(C_1-C_4)$-alkoxycarbonyl,
halo-$(C_2-C_4)$-alkenyloxymethyl,
halo-$(C_2-C_4)$-alkenyloxycarbonyl,
cyano,
halogen and
hydrogen;
R is as defined above;

(2) X is O, S or NH;
(3) Y is as defined above; and
(4) Z is preferably $(C_3-C_8)$-cycloalkyl or alternatively $(C_5-C_8)$-cycloalkenyl which are both optionally substituted as defined above.

Particularly preferred compounds of the formula 1 and their salts are those in which (1) $R^1$, $R^2$, $R^3$ and $R^4$ are identical or different radicals from the series
$(C_1-C_4)$-alkyl,
$(C_2-C_4)$-alkenyl,
$(C_1-C_4)$-alkoxy
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
R—O—CO—,
halo-$(C_1-C_4)$-alkoxymethyl,
halo-$(C_1-C_4)$-alkoxycarbonyl,
halo-$(C_2-C_4)$-alkenyloxymethyl,
halo-$(C_2-C_4)$-alkenyloxycarbonyl,
cyano,
halogen and
hydrogen;
R is as defined above;

(2) X is O or NH;
(3) Y is a bond or a bivalent hydrocarbon radical having 1 to 6 carbon atoms, in which a methylene group can be replaced by an oxygen atom, and which is optionally substituted by one or more, preferably up to three, identical or different radicals from the series
$(C_1-C_4)$-alkyl,
branched $(C_3-C_5)$-alkyl,
halo-$(C_1-C_3)$-alkyl or
halogen; and
(4) Z is $(C_3-C_6)$-cycloalkyl, which is optionally substituted as defined above.

The present invention relates to the compounds of the formula 1 in the form of the free base or of an acid addition salt. Acids which can be used for salt formation 3 are inorganic acids, such as hydrochloric acid, hydrobromic acid, nitric acid, sulfuric acid, or phosphoric acid, or organic acids such as formic acid, acetic acid, propionic acid, malonic acid, oxalic acid, fumaric acid, adipic acid, stearic acid, oleic acid, methanesulfonic acid, benzenesulfonic acid, or toluenesulfonic acid.

The compounds of the formula 1 in some cases have one or more asymmetric carbon atoms. Racemates and diastereomers can therefore occur. The invention includes both the pure isomers and mixtures thereof. The mixtures of diastereomers can be separated into the components by customary methods, e.g. by selective crystallization from suitable solvents or by chromatography. Racemates can be separated into the enantiomers by customary methods, e.g. by salt formation with an optically active acid, separation of the diastereomeric salts and release of the pure enantiomers by means of a base.

The invention furthermore relates to a process for the preparation of compounds of the formula 1, which comprises reacting compounds of the formula 2

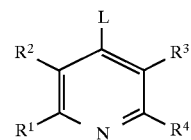

2 in which L is a leaving group and $R^1$–$R^4$ are as defined above, with the appropriate amines, alcohols, phenols or mercaptans, or :hydrogenating compounds of the formula 1 in which Z is an appropriately substituted unsaturated radical and the other radicals are as defined above, and optionally converting the compounds of the formula 1 thus obtained into their salts.

The substitution reaction described above is known in principle. The leaving group L can be varied within wide limits and can, for example, be a halogen atom such as fluorine, chlorine, bromine or iodine, or alkylthio such as methyl- or ethylthio, or alkanesulfonyloxy such as methane-, trifluoromethane- or ethanesulfonyloxy, or arylsulfonyloxy, such as benzenesulfonyloxy or toluenesulfonyloxy, or alkylsulfonyl such as methyl- or ethylsulfonyl, or arylsulfonyl such as phenyl- or toluenesulfonyl.

The compounds of the formula 2 can be prepared by known methods [e.g. J. Med. Chem. 32, 1970 (1989), J. Org. Chem. 29, 776 (1964), J. Prakt. Chem. 331, 369 (1989)]. Preferably compounds 2 in which L is Cl are employed in the preparation of the compounds 1.

The reactions with alcohols and mercaptans are carried out in the presence of a strong base such as sodium hydride, potassium hydride or potassium tert-butoxide in an inert aprotic solvent such as DMF, NMP, DMSO, THF, dioxane or sulfolane at a temperature between 0° C. and 80° C.; in the reaction with alkoxides it can also be favorable to use the accompanying alcohol as a solvent.

The conditions for the reactions of 2 with amines are dependent on the substituents $R^1$–$R^4$ in 2 and on the structure of the amines employed; if the radicals $R^1$–$R^4$ in 2 are inert, 2 can be reacted with an excess of amine to give 1 with or without solvent at temperatures between 80° and 200° C. The excess of amine can be reduced and the temperature lowered if acidic catalysts such as phenol [J. Amer. Chem. Soc. 73, 2623 (1951)] or salts such as triethylammonium chloride or ammonium chloride are used. Suitable solvent:s are e.g. DMF, N,N-dimethylacetamide, DMSO, NMP, dioxane, diethylene glycol dimethyl ether, triethylene glycol dimethyl ether, sulfolane, toluene, chlorobenzene or xylene. Mixtures of the solvents mentioned can also be used.

If one or more radicals of $R^1$–$R^4$ in 2 is or are an RO function, such as e.g. alkoxy or alkenyloxy, poor yields of 1 or other undesired reaction products are obtained by the abovementioned methods with amines; exceptions are the reactions with anilines and O-alkyl- or O-aralkyl-hydroxylamines, which lead to the products 3 and 4 (R' is a substituent of the phenyl group). Benzylamines initially yield products in with the RO function mentioned has been cleaved. These hydroxypyridines can be converted by a subsequent alkylation into the compounds analogous to 3.

The compounds of the formula 3 can be catalytically hydrogenated to give compounds of the formula 1 (scheme 1) by known methods [e.g. F. Zymalkowski, Katalytische Hydrierungen (Catalytic Hydrogenations) p. 191, Enke Verlag, Stuttgart 1965].

Scheme 1

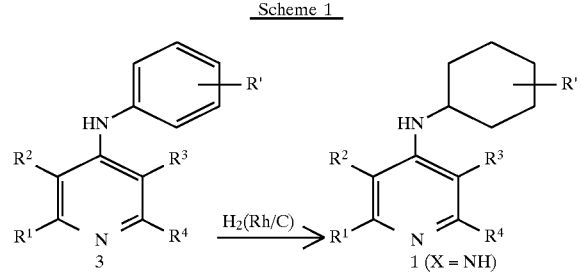

The cis/trans mixtures resulting in this way can be separated by crystallization or chromatography.

The compounds of the formula 4 are suitable intermediates for preparing a wide selection of compounds of the formula 1 where X=NH (scheme 2).

Scheme 2

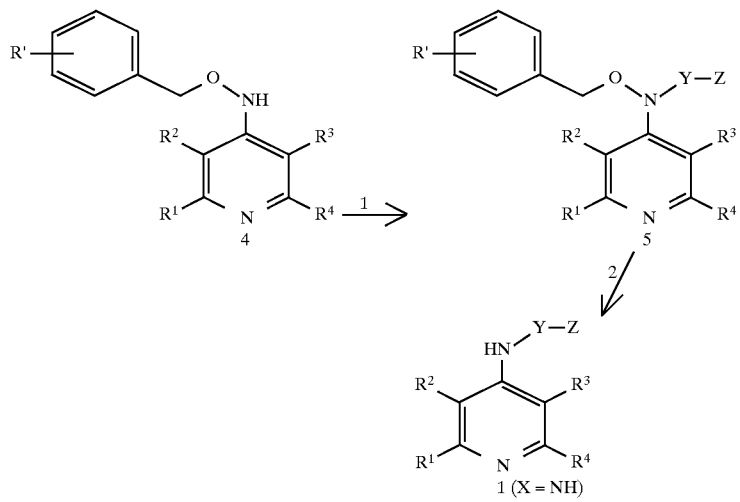

In stage 1, the products of the formula 4 are reacted selectively on the nitrogen substituent in the 4-position of the pyridine ring to give 5 using alkylating agents of the formula L-Y-Z in the presence of bases such as sodium hydride or potassium tert-butoxide; in the formula L-Y-Z L is halogen or sulfonate, Y is as defined above (apart from aryl) and Z is as indicated above. When using sterically homogeneous alkylating agents sterically homogeneous reaction products can also be obtained in this way. Solvents such as e.g. DMF, DMSO, THF, dimethoxyethane, dioxane, diethylene glycol dimethyl ether, sulfolane or toluene are employed in this reaction. Mixtures of the solvents mentioned can also be used. In stage 2 the compounds of the formula 5 are converted reductively to the compounds of the formula 1 by known methods [R. Huisgen et al. Chem. Ber. 101, 2559 (1968); C. H. Rayburn, W. R. Harlau, H. R. Haumer, Am. Soc. 72, 1721 (1950)].

The amines, alcohols and alkylating agents employed are accessible by methods known from the literature.

The alcohols can be prepared, for example, by reduction of a carbonyl group with a suitable reductant, for example a complex metal hydride or, in the case of an aldehyde or ketone, alternatively with hydrogen and a hydrogenation catalyst. Further possibilities are the reaction of an organometallic compound with a carbonyl group or an oxirane. For the preparation of cyclohexanol derivatives, suitable substituted phenols can also be reacted with hydrogen in the presence of a hydrogenation catalyst.

The amines can, for example, be prepared by reduction of an oxime or of a nitrile with a suitable reductant, for example a complex metal hydride or hydrogen, in the presence of a hydrogenation catalyst, reductive amination or Leukart-Wallach reaction of an aldehyde or ketone or Gabriel reaction of an alkyl halide or tosylate. For the preparation of cyclohexylamine derivatives suitable substituted anilines can also be reacted with hydrogen in the presence of a hydrogenation catalyst.

The compounds of the formula 1 according to the invention are distinguished by an outstanding fungicidal action. Fungal pathogens which have already penetrated into the plant tissue can be successfully controlled in a curative manner. This is particularly important and advantageous in those fungal diseases which can no longer be effectively controlled with the otherwise customary fungicides after infection has set in. The spectrum of action of the claimed compounds includes various agriculturally important, phytopathogenic fungi, such as e.g. *Phytophthora infestans, Plasmopara viticola*, but also *Erysiphe graminis, Pyrenophora teres* and *Leptosphaeria nodorum*.

The compounds according to the invention are in addition also suitable for use in industrial fields, for example as wood preservatives, as preservatives in sealing compositions, in painting colors, in cooling lubricants for metal processing or as preservatives in drilling and cutting oils.

The invention also relates to compositions which contain the compounds of the formula 1 in addition to suitable formulation auxiliaries. The compositions according to the invention in general contain the active compounds of the formula 1 to 1 to 95% by weight.

They can be formulated in various ways, using formulating agents depending on what is prespecified by the biological and/or physicochemical parameters. Possible formulations are therefore: wettable powders (WP), emulsifiable concentrates (EC), aqueous dispersions based on oil or water (SC), suspoemulsions (SC), dusting compositions (DP), seed-dressing compositions, granules in the form of water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hauser Verlag Munich, 4th Ed. 1986; van Falkenberg, "Pesticide Formulations", Marcel Dekker N.Y., 2nd Ed. 1972–73; K. Martens, "Spray Drying Handbook", 3rd Ed. 1979, G. Goodwin Ltd. London.

The formulation auxiliaries necessary such as inert materials, surfactants, solvents and other additives are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry, 2nd Ed., J. Wiley & Sons, N.Y.; Marsden, "Solvents Guide", 2nd Ed., Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface active ethylene oxide adducts] Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, combinations with other pesticidal substances, fertilizers and/or growth regulators can also be prepared, e.g. in the form of a finished formulation or as a tank-mix.

Wettable powders are preparations which are uniformly dispersible in rater, which besides the active compound and apart from a diluent or inert substance additionally contain wetting agents, e.g. polyethoxylated alkylphenols, polyethoxylated fatty alcohols, alkyl- or alkylphenolsulfonates and dispersants, e.g. sodium lignosulfonate, sodium 2,2'-dinaphthylmethane-6,6'-disulfonate, sodium dibutylnaphthalenesulfonate or alternatively sodium oleoylmethyltaurate. Emulsifiable concentrates are prepared by dissolving the active compound in an organic solvent, e.g. butanol, cyclohexanone, dimethylformamide, xylene or alternatively higher-boiling aromatics or hydrocarbons with addition of one or more emulsifiers. Examples of emulsifiers which can be used are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide-ethylene oxide-sorbitan fatty acid esters, polyoxyethylene sorbitan fatty acid esters or polyoxyethylene sorbitol esters.

Dusting compositions are obtained by grinding the active compound with finely divided solid substances, e.g. talc, natural clays such as kaolin, bentonite, poryphillite or diatomaceous earth. Granules can either be prepared by spraying the active compound onto adsorptive, granulated inert material or by applying active compound concentrates by means of adhesives, e.g. polyvinyl alcohol, sodium polyacrylate or alternatively mineral oils, to the surface of carrier substances such as sand, kaolinite or granulated inert material. Suitable active compounds can also be granulated in the manner customary for the preparation of fertilizer granules—if desired mixed with fertilizers.

In wettable powders the active compound concentration is e.g. about 10 to 90% by weight and the remainder to 100% by weight consists of customary formulation constituents. In the case of emulsifiable concentrates the active compound concentration can be about 5 to 80% by weight. Formulations in the form of dust usually contain at most 5 to 20% by weight. In the case of granules the active compound content partly depends on whether the active compound is present in liquid or solid form and which compound is present in liquid or solid form and which granulation auxiliaries, fillers etc. are used.

In addition the active compound formulations mentioned optionally contain the adhesives, wetting agents, dispersants, emulsifiers, penetrants, solvents, fillers or carriers customary in each case.

For application, the concentrates present in commercially available form are optionally diluted in a customary manner, e.g. in the case of wettable powders, emulsifiable concentrates, dispersions and in some cases also in the case of microgranules, by means of water.

Preparations in the form of dust and granulated preparations and also sprayable solutions are customarily not further diluted with other inert substances before application.

The application rate necessary varies with the external conditions such as temperature, humidity and the like. It can vary within wide limits, e.g. between 0.005 and 10.0 kg/ha or more of active substance, but it is preferably between 0.01 and 5 kg/ha.

The active compounds according to the invention can be applied, in their commercially available formulations, either on their own or in combination with other fungicides known from the literature.

Fungicides known from the literature which can be combined according to the invention with the compounds of the formula 1 and which may be mentioned are e.g. the following products:

aldimorph, andoprim, anilazine, BAS 480F, BAS 490F, benalaxyl, benodanil, benomyl, binapacryl, bitertanol, bromuconazole, buthiobate, captafol, captan, carbendazim, carboxin, CGA 173506, chlobenzthiazone, chlorthalonil, cymoxanil, cyproconazole, cyprofuram, dichlofluanid, diclomezine, diclobutrazol, diethofencarb, difenconazole (CGA 169374), difluconazole, dimethirimol, dimethomorph, diniconazole, clinocap, dithianon, dodemorph, dodine, edifenfos, ethirimol, etridiazole, fenarimol, fenfuram, fenpiclonil, fenpropidin, fenpropimorph, fentin acetate, fentin hydroxide, ferimzone (TF164), fluazinam, fluobenzimine, fluquinconazole, fluorimide, flusilazole, flutolanil, flutriafol, folpet, fosetyl-aluminum, fuberidazole, fulsulfamide (MT-F651), furalaxyl, furconazole, furmecyclox, guazatine, hexaconazole, ICI A5504, imazalil, imibenconazole, iprobenfos, iprodione, isoprothiolane, KNF 317, copper compounds such as Cu oxychloride, oxine-Cu, Cu oxide, mancozeb, maneb, mepanipyrim (KIF 3535), metconazole, mepronil, metalaxyl, methasulfocarb, methfuroxam, MON 24000, myclobutanil, nabam, nitrothalidopropyl, nuarimol, ofurace, oxadixyl, oxycarboxin, penconazole, pencycuron, PP 969, probenazole, propineb, prochloraz, procymidone, propamocarb, propiconazole, prothiocarb, pyracarbolid, pyrazophos, pyrifenox, pyrocuilon, rabenzazole, RH7592, sulfur, tebuconazole, TF 167, thiabendazole, thicyofen, thiophanate-methyl, thiram, tolclofos-methyl, tolylfluanid, triadimefon, triadimenol, tricyclazole, tridemorph, triflumizole, triforine, validamycin, vinchlozolin, XRD 563, zineb, sodium dodecylsulfonate, sodium dodecylsulfate, sodium-C13/C15 alcohol ether sulfonate, sodium cetostearyl phosphate ester, dioctylsodium sulfosuccinate, sodium isopropylnaphthalenesulfonate, sodium methylenebisnaphthalenesulfonate, cetyltrimethylammoniumchloride, salts of long-chain primary, secondary or tertiary amines, alkylpropyleneamines, laurylpyrimidinium bromide, ethoxylated quaternary fatty amines, alkyldimethylbenzylammonium chloride and 1-hydroxyethyl-2-alkylimidazoline.

The abovementioned combination components are known active compounds which, for the greatest part, are described in Ch. R Worthing, U. S. B. Walker, The Pesticide Manual, 7th Edition (1983), British Crop Protection Council.

The active compound according to the invention can moreover be present mixed with other active compounds, such as insecticides, baits, sterilants, acaricides, nematicides or herbicides, in its commercially available formulations and in the application forms prepared from these formulations. The insecticides include, for example, phosphoric acid esters, carbamates, carboxylic acid esters, fermamidines, tin compounds, substances prepared by microorganisms and others. Preferred mixture components are:

1. From the phosphorus compounds group acephate, azamethiphos, azinphos-ethyl, azinphosmethyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos, O,O-1,2,2,2-tetrachlorethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathionmethyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion.

2. From the carbamates group aldicarb, 2-sec-butylphenyl methylcarbamate (BPMG), carbaryl, carbofuran, carbosulfan, cloethocarb, benfuracarb, ethiofencarb, furathiocarb, isoprocarb, methomyl, 5-methyl-m-cumenyl butyryl(methyl)-carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio) carbamate (UC 51717).

3. From the carboxylic acid esters group allethrin, alphamethrin, 5-benzyl-3-furylmethyl-(E)-(1R) -cis-2,2-di-methyl-3-(2-oxothiolan-3-ylidenemethyl) cyclopropanecarboxylate, bioallethrin, bioallethrin ((S) -cyclopentyl isomer), bioresmethrin, biphenate, (RS)-1-cyano-1-(6-phenoxy-2-pyridyl)methyl-(1RS)-trans-3-(4-tert-butylphenyl)-2,2,-dimethylcyclopropanecarboxylate (NCI 85193), cycloprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, pheothrin ((R)-isomer), d-pralethrin, pyrethrins (natural products), resmethrin, tefluthrin, tetramethrin, tralomethrin.

4. From the amidines group amitraz, chlordimeform

5. From the tin compounds group cyhexatin, fenbutatin oxide

6. Other abamectin, Bacillus thuringiensis, bensultap, binapacryl, bromopropylate, buprofezin, camphechlor, cartap, chlorobenzilate, chlorfluazuron, 2-(4-(chlorphenyl)-4,5-diphenylthiophene (UBI-T 930), chlorfentezine, 2-naphthylmethyl cyclopropanecarboxylate (Ro12-0470), cyromazine, ethyl N-(3,5-dichloro-4-(1,1,2,3,3,3-hexafluoro-1-propoxy)phenyl)carbamoyl)-2-chlorobenzcarboximidate, DDT, dicofol, N-(N-(3,5-dichlor-4-(1,1,2,2-tetrafluorethoxy) phenylamino) carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl) (dimethyl) (3-(3-phenoxyphenyl)propyl)silane, (4-ethoxyphenyl) (3-(4-fluoro-3-phenoxyphenyl)propyl)dimethylsilane, fenoxycarb,2-fluoro-5-(4-(4-ethoxyphenyl-4-methyl)-pentyl)diphenyl ether (MTI 800), granulosis and nuclear polyhedrosis viruses, fenthiocarb, flubenzimine, flucycloxuron, flufenoxuron, gamma-HCH, hexythiazox, hydramechylnon (AG 217300), ivermectin, 2-nitromethyl-4,5-dihydro-6H-thiazine (SD 52618), 2-nitromethyl-3,4-dihydrothiazole (SD 35651), 22-nitromethylene-1,2-thiazinon-3-ylcarbamaldehyde (WL 108477), propargite, teflubenzuron, tetradifon, tetrasul, thiocyclam, triflumuron.

The active compound content of the application forms prepared from the commercially available formulations can vary within wide ranges and the active compound concentration of the application forms can be from 0.0001 up to 95% by weight of active compound, preferably between 0.001 and 1% by weight. Application takes place in a customary manner suited to the application forms.

The active compounds have good plant compatibility and favorable toxicity to warm-blooded animals and are suitable for controlling animal pests, in particular insects, arachnids, helminths and molluscs, very particularly preferably for controlling insects and arachnids which occur in agriculture, in animal breeding, in forestry, in storage and material protection and in the hygiene sector. They are effective against normally sensitive and resistant species and all or individual stages of development. The abovementioned pests include:

From the order of the Acarina e.g. *Acarus siro, Agras spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Eotetranychus spp., Oligonychus spp., Eutetranychus spp.*

From the order of the Isopoda e.g. *Oniscus asellus, Armadillidium vulgare, Porcellio scaber.*

From the order of the Diplopoda e.g. *Blaniulus guttulatus.*

From the order of the Chilopoda e.g. *Geophilus carpophagus, Scutigera spp.*

From the order of the Symphyla e.g. *Scutigerella immaculata.*

From the order of the Thysanura e.g. *Lepisma saccharina.*

From the order of the Collembola e.g. *Onychiurus armatus.*

From the order of the Orthoptera e.g. *Blatta orientalis, Periplaneta americana, Leucophaea maderae, Blattella germanica, Acheta domesticus, Gryllotalpa spp., Locusta migratoria migratcrioides, Melanoplus differentialis, Schistocerca gregaria.*

From the order of the Isoptera e.g. *Reticulitermes spp.*

From the order of the Anoplura e.g. *Phylloxera vastatrix, Pemphigus spp., Pediculus humanus corporis, Haematopinus spp., Linognathus spp.*

From the order of the Mallophaga e.g. *Trichodectes spp., Damalinea spp.*

From the order of the Thysanoptera e.g. *Hercinothrips femoralis, Thrips tabaci.*

From the order of the Heteroptera e.g. *Eurygaster spp., Dysdercus intermedius, Piesma quadrata, Cimex lectularius, Rhodnius prolixus, Triatoma spp.*

From the order of the Homoptera e.g. *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelus bilobatus, Nephotettix cincticeps, Lecanium corni, Saissetia oleae, Laodelphax striatellus, Nilaparvata lugens, Aonidiella aurantii, Aspidiotus hederae, Pseudococcus spp., Psylla spp.*

From the order of the Lepidoptera e.g. *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Laphygma exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Cacoecia podana, Capua reticulana, Choristoneura fumiferana, Clysia ambiguella, Homona magnanima, Tortrix viridana.*

From the order of the Coleoptera e.g. *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylloides chrysocephala, Epilachna varivestis, Atomaria spp., Oryzaephilus surinamensis, Anthonumus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica.*

From the order of the Hymenoptera e.g. *Diprion spp., Hoplocampa spp., Lasius spp., Monomorium pharaonis, Vespa spp.*

From the order of the Diptera e.g. *Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hypobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa.*

From the order of the Siphonaptera e.g. *Xenopsylla cheopis, Ceratophyllus spp.*

From the order of the Arachnida e.g. *Scorpio maurus, Latrodectus mactans.*

From the class of the helminths e.g. Haemonchus, Trichostrongulus, Ostertagia, Cooperia, Chabertia, Strongyloides, Oesophagostomum, Hyostrongulus, Ancylostoma, Ascaris and Heterakis and also Fasciola and plant-damaging nematodes e.g. those of the orders Meloidogyne, Heterodera, Ditylenchus, Aphelenchoides, Radopholus, Globodera, Pratylenchus, Longidorus and Xiphinema.

From the class of the gastropods, e.g. *Deroceras spp., Arion spp., Lymnaea spp., Galba spp., Succinea spp., Biomphalaria spp., Bulinus spp., Oncomelania spp.*

From the class of the bivalves e.g. *Dreissena spp.*

The invention also relates to insecticidal and acaricidal compositions which contain the compounds of the formula 1 in addition to suitable formulation auxiliaries.

The compositions according to the invention in general contain the active compounds of the formula 1 to 1 to 95% by weight.

They can be formulated in various ways, depending on what is prespecified by the biological and/or physicochemical parameters.

Suitable formulation possibilities are therefore: Wettable powders (WP), emulsifiable concentrates (EC), aqueous solutions (SC), emulsions, sprayable solutions, dispersions based con oil or water (SC), suspoemulsions (SC), dusting compositions (DP), seed-dressing compositions, granules in the form of micro-, spray-, absorption and adsorption granules, water-dispersible granules (WG), ULV formulations, microcapsules, waxes or baits.

These individual types of formulation are known in principle and are described, for example, in: Winnacker-Küchler, "Chemische Technologie" [Chemical Technology], Volume 7, C. Hauser Verlag Munich, 4th Ed. 1986; van Falkenberg "Pesticide Formulations", Marcel Dekker N.Y., 2nd Ed. 1972–73; K. Martens, "Spray Drying Handbook", 3rd Ed. 1979, G. Goodwin Ltd. London.

The formulation auxiliaries necessary such as inert materials, surfactants, solvents and other additives are likewise known and are described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts] Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, combinations with other pesticidally active substances, fertilizers and/or growth regulators can also be prepared, e.g. in the form of a finished formulation or as a tank-mix. Wettable powders are preparations which are uniformly dispersible in water, which besides the active compound and apart from a diluent or inert substance additionally contain wetting agents, e.g. polyethoxylated alkylphenols, polyethoxylated fatty alcohols, alkyl- or alkylphenolsulfonates and dispersants, e.g. sodium lignosulfonate, sodium 2,2'-dinaphthylmethane-6,6'-disulfonate, sodium dibutylnaphthalenesulfonate or alternatively sodium oleoylmethyltaurate. Emulsifiable concentrates are prepared by dissolving the active compound in an organic solvent, e.g. butanol, cyclohexanone, dimethylformamide, xylene or alternatively higher-boiling aromatics or hydrocarbons with addition of one or more emulsifiers. Examples of emulsifiers which can be used are: calcium alkylarylsulfonates such as Ca dodecylbenzenesulfonate or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan fatty acid esters, polyoxyethylene sorbitan fatty acid esters or polyoxyethylenesorbitol esters.

Dusting compositions are obtained by grinding the active compound with finely dispersed solid substances, e.g. talc, natural clays such as kaolin, bentonite, pyrophillite or diatomaceous earth. Granules can either be prepared by spraying the active compound onto adsorptive, granulated inert material or by applying active compound concentrates by means of adhesives, e.g. polyvinyl alcohol, sodium polyacrylate or alternatively mineral oils, to the surface of carrier substances such as sand, kaolinite or of granulated inert material. Suitable active compounds can also be granulated in the manner customary for the preparation of fertilizer granules—if desired mixed with fertilizers.

In wettable powders the active compound concentration is e.g. about 10 to 90% by weight and the remainder to 100% by weight consists of customary formulation constituents. In the case of emulsifiable concentrates the active compound concentration can be about 5 to 80% by weight. Formulations in the form of dust usually contain 5 to 20% by weight of actine compound, sprayable solutions about 2 to 20% by weight. In the case of granules the active compound content partly depends on whether the active compound is present: in liquid or solid form and which granulation auxiliaries, fillers etc., are used.

In addition the active compound formulations mentioned optionally contain the adhesives, wetting agents, dispersants, emulsifiers, penetrants, solvents, fillers or carriers customary in each case.

For application, the concentrates present in commercially available form are optionally diluted in a customary manner, e.g. in the case of wettable powders, emulsifiable concentrates, dispersions and in some cases also in the case of microgranules, by means of water. Preparations in the form of dust and granulated preparations and also sprayable solutions are customarily not further diluted with other inert substances before application.

The application rate necessary varies with the external conditions such as temperature, humidity and the like. It can vary within wide limits, e.g. between 0.001 and 10.0 kg/ha or more of active substance, but it is preferably between 0.005 and 5 kg/ha.

The active compounds according to the invention can be present in their commercially available formulations and in the application forms prepared from these formulations mixed with other active compounds, such as insecticides, baits, sterilants, acaricides, nematicides, fungicides, growth-regulating substances or herbicides.

The pesticides include, for example, phosphoric acid esters, carbamates, carboxylic acid esters, formamidines, tin compounds, substances produced by microorganisms and others.

Preferred mixture components are
1. from the phosphorus compounds group
   acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton-S-methyl sulfone, dialifos, diazinon, dichlorvos, dicrotophos,
   O,O-1,2,2,2-tetrachlorethyl phosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidathion, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon, vamidothion;
2. from the carbamates group
   aldicarb, 2-sec-butylphenyl methylcarbamate (BPMC), carbaryl, carbofuran, carbosulfan, cloethocarb, benfuracarb, ethiofencarb, furathiocarb, isoprocarb, methomyl, 5-methyl-m-cumenyl butyryl(methyl) carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate (OK 135), 1-methylthio-(ethylideneamino)-N-methyl-N-(morpholinothio) carbamate (UC 51717);
3. from the carboxylic acid esters group
    allethrin, alphamethirin, 5-benzyl-3-furylmethyl-(E)-(1R)-cis-2,2-di-methyl-3-(2-oxothiolan-3-ylidenemethyl) cyclopropanecarboxylate, bioallethrin, bioallethrin ((S)-cyclopentyl isomer), bioresmethrin, biphenate, (RS)-1-cyano-1-(6-phenoxy-2-pyridyl)methyl-(1RS)-trans-3-(4-tert-butylphenyl)-2,2,-dimethylcyclopropanecarboxylate (NCI 85193), cyclcoprothrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, pheothrin ((R)-isomer), d-pralethrin, pyrethrins (natural products), resmethrin, tefluthrin, tetramethrin, tralomethrin;
4. from the amidines group
    amitraz, chlordimeform;
5. from the tin compounds group
    cyhexatin, fenbutatin oxide;
6. other
    abamectin, Bacillus thuringiensis, bensultap, binapacryl, bromopropylate, buprofezin, camphechlor, cartap, chlorobenzilate, chlorfluazuron, 2-(4-(chlorphenyl)-4,5-diphenylthiophene (UBI-T 930), chlorfentezine, 2-naphthylmethyl cyclopropanecarboxylate (Ro12-0470), cyromazine, ethyl N-(3,5-dichloro-4-(1,1,2,3,3,3-hexafluoro-1-propoxy)phenyl)carbamoyl)-2-chlorobenzcarboximidate, DDT, dicofol, N-(N-(3,5-dichlor-4-(1,1,2,2-tetrafluorethoxy)phenylamino) carbonyl)-2,6-difluorobenzamide (XRD 473), diflubenzuron, N-(2,3-dihydro-3-methyl-1,3-thiazol-2-ylidene)-2,4-xylidine, dinobuton, dinocap, endosulfan, ethofenprox, (4-ethoxyphenyl) (dimethyl) (3-(3-phenoxy-phenyl)propyl)silane, (4-ethoxyphenyl) (3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), granulosis and nuclear polyhedrosis viruses, fenthiocarb, flubenzimine, flucycloxuron, flufenoxuron, gamma-HCH, hexythiazox, hydramechylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinon-3-ylcarbamaldehyde (WL 108477), propargite, teflubenzuron, tetradifon, tetrasul, thiocyclam, triflumuron.

The active compound content of the application forms prepared from the commercially available formulations can be from 0.00000001 up to 95% by weight of active compound, preferably between 0.00001 and 1% by weight.

Application is carried out in a customary manner suited to the application forms.

The active compounds according to the invention are also suitable for the control of endo- and ectoparasites in the veterinary medical field or in the field of animal raising.

The application of the active compounds according to the invention is carried out here in a known manner such as by oral application in the form of, for example, tablets, capsules, drinks, granules, by dermal application in the form, for example, of dipping, spraying, pouring-on and spotting-on and dusting as well as by parenteral application in the form, for example, of injection.

The novel compounds of the formula 1 according to the invention can therefore also be particularly advantageously employed in stock farming (e.g. cattle, sheep, pigs and poultry such as hens, geese etc.). In a preferred embodiment of the invention the novel compounds are administered to the animals orally, if appropriate in suitable formulations (cf. above) and if appropriate with the drinking water or feed. As excretion in the faeces takes place in an effective manner, the development of insects in the faeces of the animals can be very simply prevented in this way. The doses and formulations suitable in each case are in particular dependent on the species and the stage of development of the productive animals and also on the risk of infestation and can be easily determined and fixed by the customary methods. The novel compounds can be employed in cattle e.g. in doses of 0.01 to 1 mg/kg of body weight.

The following examples serve to illustrate the invention without the latter having to be restricted thereto.

A. CHEMICAL EXAMPLES

Example 1

4-(O-Benzylhydroxylamino)-3-methoxy-2-methylpyridine 16 g of 4-chloro-3-methoxy-2-methylpyridine, 63 g of phenol and 40 g of O-benzylhydroxylamine are stirred at 120° C. under nitrogen for 4 hours. After cooling, the mixture is shaken with 500 ml of 2N NaOH and $CH_2Cl_2$. The aqueous phase is extracted a second time with $CH_2Cl_2$. After concentrating the combined $CH_2Cl_2$ phases, excess O-benzylhydroxylamine is distilled off in vacuo at 0.6 mm. The residue crystallizes on stirring with hexane. After filtering off with suction and washing with hexane 21.6 g=88.4% of product remain. The product is recrystallized from ethyl acetate. M.p.: 130° C.

$^1$H-NMR (100 MHz, $CDCl_3$)=8.1 (d, 1H), 7.4 (s, 5H), 6.9 (d, 1H), 4.9 (s, 2H), 3.7 (s, 3H), 2.4 (s, 3H) ppm

Example 2

4-O-Benzylhydroxylamino-3,5-dichloropyridine hydrochloride

Prepared analogously to Example 1 from 3,4,5-trichloropyridine and O-benzylhydroxylamine.

Yield: 78%; $^1$H-NMR (100 MHz, $CDCl_3$)=8.4 (s, 2H), 7.6 (s, 1H), 7.4 (s, 5H), 5.0 (s, 2H) ppm

Example 3

4-O-Benzylhydroxylamino-3-ethoxy-2-methylpyridine

Prepared analogously to Example 1 from 4-chloro-3-ethoxy-2-methylpyridine and O-benzylhydroxylamine.

Yield: 67%; $^1$H-NMR (100 MHz, $CDCl_3$)=8.1 (d, 1H), 7.4 (s, 5H), 6.9 (d, 1H), 4.9 (s, 2H), 3.8 (q, 2H), 2.4 (s, 3H), 1.3 (t, 3H) ppm

Example 4

4-[O-Benzyl-N-(4-cis-tert-butylcyclohexyl)] hydroxylamino-3-ethoxy-2-methylpyridine hydrochloride 5.2 g of 4-O-benzylhydroxylamino-3-ethoxy-2-methylpyridine (from Example 3) in 4.0 ml of abs. THF are added under nitrogen to a solution of 2.4 g of potassium tert-butoxide in 20 ml of abs. DMSO. A solution of 7.2 g of trans-1-(3-nitrophenylsulfonyloxy)-4-tert-butylcyclohexane in 40 ml of abs. THF is then added dropwise. After 6 hours, the THF is distilled off in vacuo and the mixture is extracted with methylene chloride after addition of water. Chromatography of the methylene chloride phase on silica gel with ethyl acetate yields 4.7 g=52% of product. Using ethereal HCl, the hydrochloride precipitates from ether in solid form.

$^1$H-NMR (100 MHz, CDCl$_3$)=8.1 (t, 1H), 7.4 (d, 1H), 7.3 (s, 5H), 4.8 (s, 2H), 4.4 (m, 1H), 4.0 (q, 2H), 2.7 (s, 3H), 1.4–2.0 (m, 9H), 1.4 (t, 3H), 0.8 (s, 9H) ppm

Example 5

4-[O-Benzyl-N-(4-cis-tert-butylcyclohexyl)] hydroxylamino-3-methoxy-2-methylpyridine hydrochloride Prepared analogously to Example 4 from 4-(O-benzylhydroxylamino)-3-methoxy-2-methylpyridine (from Example 1) and trans-1-(3-nitrophenylsulfonyloxy)-4-tert-butylcyclohexane Yield: 26%; $^1$H-NMR (100 MHz, DMSO)=8.3 (t, 1H), 7.5 (d, 1H), 7.4 (m, 5H), 4.5 (m, 1H), 3.8 (s, 3H), 2.4 (s, 3H), 0.8–2.1 (m, 9H), 0.8 (s, 9H) ppm.

Example 6

4-[O-Benzyl-N-(4-cis-ethylcyclohexyl)] hydroxylamino-3-methoxy-2-methylpyridine

Prepared analogously to Example 4 from 4-(O-benzylhydroxylamino)-3-methoxy-2-methylpyridine (from Example 1) and trans-1-(3-nitrophenylsulfonyloxy)-4-ethylcyclohexane Yield: 80%; $^1$H-NMR (100 MHz, CDCl$_3$)=8.1 (d, 1H), 7.3 (s, 5H), 7.1 (d, 1H), 4.6 (s, 2H), 3.8 (s, 3H), 3.6 (m, 1H), 2.5 (s, 3H), 1.2–2.0 (m, 11H), 0.9 (t, 3H) ppm

Example 7

4-[O-Benzyl-N-(4-cis-tert-butylcyclohexyl)] hydroxylamino-3,5-dichloropyridine hydrochloride Prepared analogously to Example 4 from 4-(O-benzylhydroxylamino)-3,5-dichloropyridine and trans-1-(3-nitrophenylsulfonyloxy)-4-tert-butylcyclohexane Yield: 34%; $^1$H-NMR (100 MHz, CDCl$_3$)=8.3 (s, 2H), 7.2 (m, 5H), 4.8 (s, 2H), 3.9 (m, 1H), 0.9 (s, 9H), 0.8–2.4 (m, 9H) ppm

Example 8

4-[O-Benzyl-N-(4-trans-tert-butylcyclohexyl)] hydroxyl-amino-3-ethoxy-2-methylpyridine hydrochloride 2.5 g of solid potassium t-butoxide are added in portions to 5.2 g of 4-O-benzylhydroxylamino-3-ethoxy-2-methylpyridine (from Example 3) in 50 ml of abs. DMSO. When everything is dissolved, 7.6 g of cis-1-tosyloxy-4-tert-butylcyclohexane are likewise added in portions. After 17 hours, the mixture is poured into sodium chloride solution and extracted with ethyl acetate. The ethyl acetate phase is concentrated and chromatographed on silica gel. The product is further purified by precipitating the hydrochloride from ether. 4.1 g=45%

$^1$H-NMR (100 MHz, CDCl$_3$)=8.0 (t, 1H), 7.4 (d, 1H), 7.4 (s, 5H), 4.9 (m, 1H), 4.3–3.9 (m, 3H), 2.6 (s, 3H), 1.4 (t, 3H), 0.8 (s, 9H), 0.9–2.1 (m, 9H) ppm

Example 9

4(4-cis-tert-Butylcyclohexylamino)-3-ethoxy-2-methyl-pyridine 4.7 g of 4-[O-benzyl-N-(4-cis-tert-butylcyclohexyl)] hydroxylamino-3-ethoxy-2-methylpyridine (from Example 4) in 50 ml of methanol are hydrogenated with about 2 g of moist Raney nickel at normal pressure until absorption of hydrogen is complete. After filtering, the filtrate is concentrated to dryness. The residue is dissolved in ether and the hydrochloride is precipiptated using ethereal HCl. After filtering off and washing with ether, the amine is liberated from the hydrochloride using sodium bicarbonate solution. 2.9 g=96%

$^1$H-NMR (100 MHz, CDCl$_3$)=7.9 (d, 1H), 6.3 (d, 1H), 4.8 (d, 1H), 3.9 (q, 2H), 3.7 (m, 1H), 2.5 (s, 3H), 1.4 (t, 3H), 0.9 (s, 9H), 1.0–2.0 (m, 9H) ppm

Example 10

4-(4-cis-tert-Butylcyclohexylamino)-3-methoxy-2-methylpyridine

Prepared analogously to Example 9 from 4-[O-benzyl-N-(4-cis-tert-butylcyclohexyl)]hydroxylamino-3-methoxy-2-methylpyridine (from Example 5).

$^1$H-NMR (100 MHz, CDCl$_3$)=7.9 (d, 1H), 6.4 (d, 1H), 4.8 (d, 1H), 3.7 (s, 3H), 3.7 (m, 1H), 2.4 (s, 3H), 0.9 (s, 9H), 1.0–2.0 (m, 9H) ppm

Example 11

4-(4-cis-Ethylcyclohexylamino)-3-methoxy-2-methylpyridine hydrochloride

Prepared analogously to Example 9 from 4-[O-benzyl-N-(4-cis-ethylcyclohexyl)]hydroxylamino-3-methoxy-2-methylpyridine (from Example 6).

$^1$H-NMR (100 MHz, CDCl$_3$) 8.0 (t, 1H), 6.4 (d, 1H), 5.8 (d, 1H), 3.8 (s, 3H), 3.8 (m, 1H), 2.7 (s, 3H), 1.1–2.1 (m, 9H), 0.9 (t, 3H) ppm

Example 12

4-(4-trans-tert-Butylcyclohexylamino)-3-ethoxy-2-methylpyridine

Prepared analogously to Example 9 from 4-[O-benzyl-N-(4-trans-tert-butylcyclohexyl)]hydroxylamino-3-ethoxy-2-methylpyridine (from Example 8)

$^1$H-NMR (100 MHz, CDCl$_3$)=7.9 (d, 1H), 6.4 (d, 1H), 4.4 (d, 1H), 3.8 (q, 2H), 3.1 (m, 1H), 2.4 (s, 3H), 1.4 (t, 3H), 0.9 (s, 9H), 1.0–2.2 (m, 9H) ppm

Example 13

4-(4-cis-tert-Butylcyclohexylamino)-3,5-dichloropyridine 3 g of 4-O-Benzylhydroxylamino-3,5-dichloropyridine hydrochloride (from Example 7) in 10 ml of methanol and 3 ml of glacial acetic acid are stirred with 2 g of zinc dust. After 17 hours the mixture is filtered. The residue which remains after concentrating is shaken with sodium hydroxide solution and methylene chloride. The methylene chloride phase is purified on silica gel. The eluent used is ethyl acetate to which increasing amounts of methanol are added. 0.7 g=34%

$^1$H-NMR (100 MHz, CDCl$_3$)=8.2 (s, 2H), 5.0 (m, 1H), 4.5 (m, 1H), 1.0–2.0 (m, 9H), 0.8 (s, 3H) ppm

Example 14

2-Methyl-3-chloro-4-(4-cis-tert-butylcyclohexylamino)pyridine 1.62 g (10 mmol) of 2-methyl-3,4-dichloropyridine, 3.11 g (20 mmol) of 4-cis-tert-butylcyclohexylamine and 0.2 g of ammonium chloride are warmed at 180° C. for 10 hours in 5 ml of N-methylpyrrolidone. For working up, saturated sodium bicarbonate solution is added and the mixture is extracted with ethyl acetate. The reaction product is purified by chromatography ($SiO_2$; EtOAc).

Yield: 1.5 g (53.4%); $^1$H-NMR ($CDCl_3$)=8.0 (d, 1H), 6.4 (d, 1H), 5.0 (d, 1H), 3.7 (m, 1H), 2.5 (s, 3H), 0.9–2.1 (m, 9H), 0.9 (s, 9H) ppm

Example 15

2-Methyl-3-methoxy-4-(4-cis-tert-butylcyclohexyloxy)pyridine

A mixture of 1.57 g (10 mmol) of 2-methyl-3-methoxy-4-chloropyridine, 2.03 g (13 mmol) of 4-cis-tert-butylcyclohexanol and 15 ml of DMSO is added dropwise at 25° C. to 0.36 g (12 mmol) of NaH (80% strength) in 25 ml of DMSO. The mixture is then stirred at 60° C. for 7 hours. For working up, saturated ammonium chloride solution is added at 20°–25° C. and the mixture is extracted with ethyl acetate. The reaction product is purified by chromatography ($SiO_2$; EtOAc).

Yield: 1.26 g (45.6%); $^1$H-NMR ($CDCl_3$)=8.1 (d, 1H), 6.7 (d, 1H), 4.6 (m, 1H), 3.9 (s, 3H), 2.5 (s, 3H), 0.9–2.3 (m, 9H), 0.9 (s, 9H) ppm

Example 16

3,5-Dichloro-4-(-cis-tert-butylcyclohexyloxy)pyridine

A mixture of 1.82 g (10 mmol) of 3,4,5-trichloropyridine, 2.03 g (13 mmol) of 4-cis-tert-butyl-cyclohexanol and 15 ml of DMSO is added dropwise at 25° C. to 0.36 g (12 mmol) of NaH (80% strength) in 25 ml of DMSO. The mixture is then stirred at 70° C. for 20 hours. For working up, saturated ammonium chloride solution is added at 20°–25° C. and the mixture is extracted with ethyl acetate. The reaction product is purified by chromatography ($SiO_2$; hexane/diisopropyl ether [1:3]).

Yield: 2.23 g (74%); $^1$H-NMR ($CDCl_3$)=8.4 (s, 2H), 4.3 (m, 1H), 0.9–2.3 (m, 9H), 0.8 (s, 9H) ppm

Example 17

2-Methyl-3-chloro-4-(4-cis-tert-butyl-cyclohexyloxy)pyridine

A mixture of 1.62 g (10 mmol) of 1-methyl-3,4-dichloropyridine, 2.03 g (13 mmol) of 4-cis-tert-butylcyclohexanol and 30 ml of DMSO is added dropwise to 0.36 g (12 mmol) of NaH (80% strength) in 25 ml of DMSO. The mixture is then stirred at 40° C. for 1.5 hours and at 60° C. for 5 hours. For working up, saturated ammonium chloride is added at 20°–25° C. and the mixture is extracted with ethyl acetate. The reaction product is purified by chromatography ($SiO_2$; diisopropyl ether/EtOAc [5:1]).

Yield: 1.71 g (60.7%); M.p.: 102°–104° C.; $^1$H-NMR ($CDCl_3$)=8.2 (d, 1H), 6.7 (d, 1H), 4.2 (m, 1H), 2.6 (s, 3H), 0.9–2.3 (m, 9H), 0.9 (s, 9H) ppm

Example 18

2,6-Dimethyl-4-(4-cis-tert-butylcyclohexylamino)pyridine

Was prepared analogously to Example 14 from 2,6-dimethyl-4-chloropyridine and 4-cis-tert-butylcyclohexylamine.

Example 19

4-[O-Benzyl-N-(4-cis-tert-butylcyclohexyl)]hydroxylamino-1,3-dimethoxy-2-ethylpyridinium iodide 7.2 g of 4-[O-benzyl-N-(4-cis-tert-butylcyclohexyl)]hydroxylamino-3-methoxy-2-methylpyridine (Example 5) in 50 ml of $CH_2Cl_2$ are stirred with 6 g of 70% strength meta-chloroperbenzoic acid for 2 hours. The solution is then washed with sodium bisulfite solution and sodium hydrogencarbonate solution. After concentrating, 4.8 g=56% of N-oxide are obtained from hexane.

The material is dissolved in 100 ml of abs. THF and treated at −75° C. with 8.5 ml of 1.6 molar butyllithium solution in hexane. After 2 hours at −75° C., 5.3 ml of methyl iodide are added to the solution and it is allowed to come to room temperature. After 4 hours, it is concentrated and the product is purified on silica gel using ethyl acetate/glacial acetic acid 20:1. 2.7 g=39%.

$^1$H-NMR (100 MHz, DMSO)=8.0 (d, 1H), 7.3 (s, 5H), 7.3 (d, 1H), 4.7 (s, 2H), 3.9 (s, 3H), 3.7 (m, 1H), 3.3 (s, 3H), 2.9 (q, 2H), 1.1 (t, 3H), 0.8 (s, 9H), 1.2–2.0 (m, 9H) ppm

Example 20

4-(4-cis-tert-Butylcyclohexylamino)-2-ethyl-3-methoxypyridine hydrochloride 2.7 g of 4-[O-benzyl-N-(4-cis-tert-butylcyclohexyl)]-hydroxylamino-1,3-dimethoxy-2-ethylpyridinium iodide (Example 19) in 100 ml of methanol are hydrogenated using 2 g of Raney nickel. After filtering and concentrating, the residue is shaken with sodium hydroxide solution and ethyl acetate. The organic phase is separated off, dried with sodium sulfate and concentrated. The syrup which remains is dissolved in hexane and the hydrochloride is precipitated using ethereal HCl. 1.5 g=95%.

$^1$H-NMR (100 MHz, $CDCl_3$)=8.0 (t, 1H), 6.7 (d, 1H), 5.8 (d, 1H), 3.8 (s, 3H), 3.8 (m, 1H), 3.0 (q, 2H), 1.5 (t, 3H), 0.9 (s, 9H), 1.1–2.1 (m, 9H) ppm

Example 21

4-(4-cis-tert-Butylcyclohexylamino)pyridine

Prepared analogously to Example 14 from 4-chloropyridine and 4-cis-tert-butylcyclohexylamine.

Yield: 73% M.p.: 137° C.; $^1$H-NMR ($CDCl_3$)=8.2 (m, 2H), 6.4 (m, 2H), 4.4 ("d", 1H), 3.7 (m, 1H), 0.9–2.1 (m, 9H), 0.9 (s, 9H) ppm

Example 22

4-(4-tert-Butylbenzylamino)-3-methoxy-2-methylpyridine hydrochloride 7.9 g of 4-chloro-3-methoxy-2-methylpyridine, 20 g of phenol and 10 g of 4-tert-butylbenzylamine are stirred at 155°–160° C. until the 4-chloro-3-methoxy-2-methylpyridine has disappeared. The phenol and the residual benzylamine are distilled off in vacuo, and the residue is shaken with sodium hydroxide solution and ethyl acetate. The ethyl acetate extract is concentrated. On stirring with acetone 4.5 g=31% of crystals of 4-(4-tert-butylbenzylamino)-3-hydroxy-2-methylpyridine are obtained. These are dissolved in 100 ml of methanol and stirred with diazomethane solution until evolution of nitrogen has ended. After concentrating the product is purified by chromatography on silica gel (acetone/methanol 2:1).

The crude product is dissolved in ether. On addition of ethereal HCl the hydrochloride precipitates. 3.2 g=64%.

$^1$H-NMR (100 MHz, CDCl$_3$)=7.9 (t, 1H), 7.3 (m, 4H), 6.6 (d, 1H), 4.5 (d, 2H), 3.9 (s, 3H), 2.7 (s, 3H), 1.3 (s, 9H) ppm

Example 23

4-[4-cis-tert-Butylcyclohexylmethylamino]-3-methoxy-2-methylpyridine 1.3 g of 4-(4-cis-tert-butylbenzylamino)-3-methoxy-2-methylpyridine (Example 22) in 40 ml of methanol and 3 ml of 2N HCl are hydrogenated using 1 g of rhodium on alumina. After the absorption of 290 ml of hydrogen the mixture is filtered and the filtrate is concentrated. The residue is shaken with 2N NaOH and methylene chloride. The methylene chloride phase concentrated and stirred with hexane, whereupon 0.3 g=22% of the cis-isomer crystallize. The mother liquor largely contains transisomer.

$^1$H-NMR (100 MHz, CDCl$_3$)=8.0 (d, 1H), 6.4 (d, 1H), 4.6 (m, 1H), 3.6 (s, 3H), 3.1 (3, 2H), 2.4 (s, 3H), 0.9 (s, 9H), 1.0–1.9 (m, 10H) ppm

Example 24

3-bromo-4-[4-cis-(1-methylpropyl)cyclohexyl]amino-2-methylpyridine 2.2 g of 3-bromo-4-chloro-2-methylpyridine and 2.3 g of 4-(1-methylpropyl:cyclohexylamine are heated at 150° C. for 4.5 hours with 88 mg of ammonium chloride in 8.5 ml of N-methylpyrrolidone. After cooling the mixture is poured into 40 ml of concentrated NaHCO$_3$ solution and the product is extracted with ethyl acetate. The cis/trans mixture is then freed from impurities by chromatography on silica gel using ethyl acetate/heptane 1:1. The isomers are then separated by chromatography on Sephadex using methanol.

Yield: 200 mg=5% trans-isomer 330 mg=cis-isomer; $^1$H-NMR [100 MHz CDCl$_3$] (cis-isomer) δ: 8.0 (d, 1H), 6.3 (d, 1H), 5.1 (d, 1H), 3.7 (m, 1H), 2.6 (s, 3H), 0.8–1.9 (m, 18H) ppm

Example 25

3-Chloro-4-(4-cis-tert-butylcyclohexylamino)-2-methylpyridine 1.2 g of 3,4-dichloro-2-methylpyridine and 1.3 g of 4-cis-tert-butylcyclohexylamine are heated at 180° C. in 7 ml of N-methylpyrrolidone for 4 hours together with 55 g of ammonium chloride. After cooling, the mixture is poured into saturated sodium bicarbonate solution and extracted several times with ethyl acetate. The product is chromatographed on silica gel using ethyl acetate/heptane 1:1.

Yield 420 mg=20%; $^1$H-NMR (100 MHz, CDCl$_3$) δ: 8.0 (d, 1H), 6.4 (d, 1H), 5.0 (d, 1H), 3.7 (m, 1H), 2.5 (s, 3H), 1.0–2.1 (m, 9H), 0.9 (s, 9H) ppm

Example 26

3-Bromo-4-(4-cis-tert-butylcyclohexylamino)-2-methylpyridine

Was prepared analogously to Example 25 from 3-bromo-4-chloro-2-methylpyridine and 4-cis-tert-butylcyclohexylamine.

Yield: 13%; $^1$H-NMR (100 MHz, CDCl$_3$) δ: 8.0 (d, 1H), 6.3 (d, 1H), 5.1 (m, 1H), 3.7 (m, 1H), 2.6 (s, 3H), 1.0–2.0 (m, 9H), 0.9 (s, 9H) ppm

Example 27

3-Chloro-4-[4-cis-tert-butylcyclohexylamino]-2-ethylpyridine

Was prepared analogously to Example 25 from 3,4-dichloro-2-ethylpyridine and 4-cis-tert-butylcyclohexylamine.

Yield: 22%; $^1$H-NMR (100 MHz, CDCl$_3$) δ: 8.1 (d, 1H), 6.4 (d, 1H), 5.1 (d, 1H), 3.7 (m, 1H), 2.9 (q, 2H), 1.3 (t, 3H), 1.0–2.1 (m, 9H), 0.9 (s, 9H) ppm

Example 28

3-Chloro-4-[4-cis-4-(1-methylpropyl)cyclohexyloxy]-2-methylpyridine 1.6 g of 3,4-dichloro-2-methylpyridine and 1.7 g of 4-cis-(1-methylpropyl)cyclohexanol in 4 ml of DMSO are added dropwise to 330 mg of sodium hydride in 30 ml of DMSO. The mixture is stirred at 40° C. for 105 minutes. After cooling, ammonium chloride solution is added dropwise until the pH is 7. The mixture is then shaken with ethyl acetate and water. The organic phase is purified on silica gel using ethyl acetate/heptane 7:3.

Yield : 53%; $^1$H-NMR (100 MHz, CDCl$_3$) δ: 8.2 (d, 1H), 6.7 (d, 1H), 4.7 (m, 1H), 2.6 (s, 3H), 0.8–2.2 (m, 18H) ppm

Example 29

2-Ethyl-3-bromo-4-(cis-4-tert-butylcyclohexylamino)pyridine 3.09 g (20 mmol) of 4-tert-butyl-cyclohexanone in 3.3 ml of ethanol are treated with 3.3 ml of triethyl orthoformate and 2 drops of boron trifluoride etherate and the mixture is warmed at 50° C. for 30 min. After the addition of 2.1 g (10 mmol) of 2-ethyl-3-bromo-4-aminopyridine, the reaction mixture is heated with simultaneous removal by distillation of the low-boiling components at 135°–140° C. for 3.5 hours. It is then cooled, 40 ml of 1,2-dichloroethane, 3.18 g (15 mmol) of sodium triacetoxyborohydride and 0.57 ml (10 mmol) of glacial acetic acid are added and the mixture is warmed at 50°–60° C. for 3 hours; the reaction mixture is then cooled, saturated aqueous sodium hydrogen carbonate solution is added, the 1,2-dichloroethane is evaporated and the reaction product is extracted from the aqueous phase with ethyl acetate. Purification is carried out by column chromatography.

Yield: 1.55 g (46%); oil; R$_F$: 0.49 (EtOAc) δ: 8.08 (d, 1H), 6.30 (d, 1H), 5.15 (d, 1H), 3.75 (m, 1H), 2.90 (9, 2H), 1.28 (t, 3H), 0.88 (s, 9H), 1.0–2.0 (m, 9H) ppm

Example 30

2-Ethyl-3-bromo-4-(trans-4-tert-butylcyclohexylamino)pyridine

As Example 29

Yield: 0.5 g (14 %), R$_F$=0.58 (EtOAc); $^1$H-NMR (CDCl$_3$) δ: 8.1 (d, 1H), 6.32 (d, 1H), 4.68 (d, 1H), 3.20 (m, 1H), 2.90 (q, 2H), 1.30 (t, 3H), 0.90 (s, 9H), 1.0–2.2 (m, 9H) ppm.

Example 31

2-Chloro-3-bromo-4-(cis-4-tert-butylcyclohexylamino)pyridine 2.2 g (10 mmol) of 2,4-dichloro-3-bromopyridine, 1.86 g (12 mmol) of cis-4-tert-butylcyclohexylamine and 0.1 g ammonium chloride are warmed at 120° C. for 8 hours in 10 ml of N-methylpyrrolidone. After cooling, saturated aqueous sodium hydrogencarbonate solution is added and the reaction product extracted with ethyl acetate. Purification is carried out by column chromatography.

Yield: 1.28 g (37%); $R_F$: 0.41 (diisopropyl ether); $^1$H-NMR (CDCl$_3$) δ 7.92 (d, 1H), 6.38 (d, 1H), 5.27 (d, 1H), 3.74 (m, 1H), 1.0–2.0 (m, 9H), 0.89 (s, 9H) ppm

Example 32

2-Methoxy-3-bromo-4-(cis-4-tert-butylcyclohexylamino)pyridine 1.73 g (5 mmol) of 2-chloro-3-bromo-4-(cis-4-tert-butylcyclohexylamino)pyridine and 3.67 ml (20 mmol) of sodium methoxide in methanol (30% strength) in 20 ml of DMF are warmed at 80° C. for 1 hour. After cooling, water is added, the mixture is adjusted to pH 8 with ½ conc. HCl and the reaction product is extracted with ethyl acetate. For purification it is chromatographed.

Yield: 1.48 g (87%); $R_F$=0.87 (diisopropyl ether); $^1$H-NMR (CDCl$_3$) δ 7.76 (d, 1H), 6.22 (d, 1H), 5.08 (d, 1H), 3.95 (s, 3H), 3.75 (m, 1H), 1.0–2.0 (m, 9H), 0.87 (s, 9H) ppm

Example 33

2,3-Dimethoxy-4-(cis-4-tert-butylcyclohexylamino)pyridine

Analogously to Example 29 from 2,3-dimethoxy-4-aminopyridine.

The product prepurified by column chromatography is taken up in diisopropyl ether and treated with ethereal hydrochloric acid. The precipitated hydrochloride of the reaction product is filtered off with suction and purified by crystallization from acetone; subsequent treatment with 2N sodium hydroxide solution and extraction with ethyl acetate yields pure cis product.

Yield: 46%; $R_F$=0.66 (diisopropyl ether); $^1$H-NMR (CDCl$_3$); δ 7.65 (d, 1H), 6.25 (d, 1H), 4.86 (d, 1H), 3.96 (s, 3H), 3.80 (s, 3H), 3.67 (m, 1H), 1.0–2.0 (m, 9H), 0.86 (S, 9H) ppm.

Example 34

2-Chloro-3-methoxy-4-(cis-4-tert-butylcyclohexylamino)pyridine
as Example 29, but using 1.58 g (10 mmol) of 2-chloro-3-methoxy-4-aminopyridine instead of 2-ethyl-3-bromo-4-aminopyridine.

Yield: 1.2 g (41%); $R_F$: 0.58 g (diisopropyl ether); $^1$H-NMR (CDCl$_3$) δ 7.80 (d, 1H), 6.43 (d, 1H), 5.00 (d, 1H), 3.85 (s, 3H), 3.68 (m, 1H), 1.0–2.0 (m, 9H), 0.88 (s, 9H) ppm.

Example 35

2-Chloro-3-methoxy-4-(trans-4-tert-butylcyclohexylamino)pyridine
as Example 34
Yield: 0.4 g (14%); $R_F$=0.72 g (diisopropyl ether); $^1$H-NMR (CDCl$_3$) δ 7.80 (d, 1H), 6.44 (d, 1H), 4.66 (d, 1H), 3.80 (s, 3H), 3.18 (m, 1H), 1.0–2.2 (m, 9H), 0.88 (s, 9H) ppm.

Example 36

2-Ethyl-4-(4-tert-butyl-cyclohexylamino)pyridine
as Example 29, but using 1.22 g (10 mmol) of 2-ethyl-4-aminopyridine instead of 2-ethyl-3-bromo-4-aminopyridine.

Yield: 0.83 g (32%); $R_F$=0.64 (acetone: CH$_2$Cl$_2$: CH$_3$OH: EtOAc: H$_2$O: AcOH=9:6:2:2:2:1)
Substitution on the cyclohexyl radical: cis/trans=3:1
$^1$H-NMR (CDCl$_3$) [cis-cpd.] δ 8.12 (d, 1H), 6.39 (s, 1H), 6.34 (d, 1H), 4.26 (d, 1H), 3.72 (m, 1H), 2.66 (q, 2H), 1.0–2.2 (m, 9H), 1.24 (t, 3H), 0.87 (s, 9H) ppm. $^1$H-NMR (CDCl$_3$) [trans-cpd.] δ 8.10 (d, 1H), 6.39 (s, 1H), 6.36 (d, 1H), 3.96 (d, 1H), 3.18 (m, 1H), 2.66 (q, 2H), 1.0–2.2 (m, 9H), 1.24 (t, 3H), 0.88 (s, 9H) ppm.

Example 37

2-Isopropyl-4-(4-tert-butyl-cyclohexylamino)pyridine
as Example 29, but using 1.36 g (10 mmol) of 2-isopropyl-4-amino-pyridine instead of 2-ethyl-3-bromo-4-aminopyridine.

Yield: 1.55 g (57%); $R_F$=0.62 (acetone: CH$_2$Cl$_2$: CH$_3$OH: EtOAc: H$_2$O: AcOH=9:6:2:2:2:1)
Substitution on the cyclohexyl radical: cis/trans=72:28
$^1$H-NMR (CDCl$_3$) [cis-cpd.] δ 8.12 (d, 1H), (s, 1H), 6.24 (d, 1H), 4.26 (d, 1H), 3.72 2(m, 1H), 2.89 (m, 1H), 1.0–2.2 (m, 9H), 1.26 (d, 6H), 0.87 (s, 9H) ppm. $^1$H-NMR (CDCl$_3$) [trans-cpd.] δ 8.10 (d, 1H), 6.30 (s, 1H), 6.26 (d, 1H), 3.98 (d, 1H), 3.20 (m, 1H), 2.89 (m, 1H), 1.0–2.2 (m, 9H), 1.25 (d, 6H), 0.87 (s, 9H) ppm.

Example 38

3-Chloro-2-isopropyl-4-(4-cis-tert-butyl-cyclohexylamino)pyridine
was prepared analogously to Example 29 starting from 4-amino-3-chloro-2-isopropylpyridine and 4-tert-butylcyclohexanone Yield: 44.9%; $^1$H-NMR (CDCl$_3$) δ: 8.1 (d, 1H), 6.4 (d, 1H), 5.1 (d, 1H), 3.7 (m, 1H), 3.5 (m, 1H), 1.0–2.0 (m, 15H), 0.9 (s, 9H) ppm

Example 39

2-Chloro-4-(cis-4-tert-butyl-cyclohexylamino)pyridine
as Example 31, from 2,4-dichloropyridine
Yield: 30%; M.p.: 109° C.; $^1$H-NMR (CDCl$_3$) δ: 7.90 (d, 1H), 6.44 (s, 1H), 6.34 (d, 1H), 4.48 (d, 1H), 3.66 (m, 1H), 1.0–2.0 (m, 9H), 0.86 (s, 9H) ppm.

Example 40

2-Methoxy-4-(cis-4-tert-butylcyclohexylamino)pyridine
as Example 32, from 2-chloro-4-(cis-4-tert-butylcyclohexylamino)pyridine
Yield: 90%; $R_F$=0.30 (diisopropyl ether); $^1$H-NMR (CDCl$_3$) δ: 7.76 (d, 1H), 6.15 (d, 1H), 5.84 (s, 1H), 4.39 (d, 1H), 3.87 (s, 3H), 3.64 (m, 1H), 1.0–2.0 (m, 9H), 0.85 (s, 9H) ppm.

Example 41

3-Methoxy-4-(4-tert-butyl-cyclohexylamino)pyridine
as Example 29, using 3-methoxy-4-aminopyridine
Yield: 23%; Cis/trans ratio of the substituents on the cyclohexane ring: 72:28 $^1$H-NMR (CDCl$_3$) δ: 7.8–8.08 (s,d, 2H) 6.43 (d, 1H), 4.85 and 4.53 (d, 1H), 3.91 and 3.88 (s, 3H), 3.68 and 3.18 (m, 1H), 1.0–2.2 (m, 9H), 0.87 (s, 9H) ppm.

B. FORMULATION EXAMPLES a) A dusting composition is obtained by mixing 10 parts by weight of active compound and 90 parts by weight of talc as inert substance and comminuting in a hammer mill.

b) A wettable powder which is easily dispersible in water is obtained by mixing 25 parts by weight of active compound, 65 parts by weight of kaolin-containing quartz as inert substance, 10 parts by weight of potassium lignosulfonate and one part by weight of sodium oleoylmethyltaurate as wetting agent and dispersant and grinding in a pinned disc mill.

c) A dispersion concentrate which is easily dispersible in water is prepared by mixing 40 parts by weight of active compound with 7 parts by weight of a sulfosuccinic acid monoester, 2 parts by weight of a sodium lignosulfonate and 51 parts by weight of water and grinding in a friction ball mill to a fineness of less than 5 microns.

d) An emulsifiable concentrate can be prepared from 15 parts by weight of active compound, 75 parts by weight of cyclohexanone as solvent and 10 parts by weight of ethoxylated nonylphenol (10 EO) as emulsifier.

e) Granules can be prepared from 2 to 15 parts by weight of active compound and an inert granule carrier material such as attapulgite, pumice granules and/or quartz sand. Expediently a suspension of the wettable powder from Example b) having a solid content of 30 is used and this is sprayed onto the surface of attapulgite granules, dried and mixed intimately. The weight content of the wettable powder here is about 5% and that of the inert carrier material about 95% of the finished granules.

C. BIOLOGICAL EXAMPLES

Example 1

*Phytophthora infestans*

Tomato plants of the variety "Rheinlands Ruhm" were uniformly wetted in the 3 to 4 leaf stage until dripping wet with aqueous suspensions of the claimed compounds. After drying, the plants were inoculated with a zoosporangia suspension of *Phytophthora infestans* and kept for 2 days under optimum infection conditions in a climatic chamber. Cultivation of the plants was then continued in the greenhouse until expression of symptoms. The assessment of attack was carried out about 1 week after inoculation. The degree of attack on the plants was expressed in % of attacked leaf area in comparison with the untreated, 100% infected control plants.

With 250 mg of active compound/l of spray liquor the following substances show a complete suppression of attack:
Compounds from Examples 10 and 11

Example 2

*Plasmopara viticola*

Grape seedlings of the varieties "Riesling/Ehrenfelder" were treated until dripping wet with aqueous suspensions of the claimed compounds about 6 weeks after sowing. After drying of the spray coating the plants were inoculated with a zoosporangia suspension of *Plasmopara viticola* and placed dripping wet for 4 to 5 hours in a climatic chamber at 23° C. and 80 to 90% rel. atmospheric humidity.

After an incubation time of 7 days in the greenhouse, the plants were again placed in the climatic chamber overnight in order to stimulate the sporulation of the fungus. Assessments of attack were then carried out. The degree of attack was expressed in % of attacked leaf area in comparision with the untreated, 100% infected control plants.

With 250 mg of active compound/l of spray liquor the following substances show a complete suppression of attack:
Compounds from Examples 15, 10 and 20

Example 3

*Pyrenophora teres*

Barley plants of the variety "Igri" were treated in the 2-leaf stage until dripping wet with an aqueous suspension of the claimed compounds. After drying of the spray coating the plants were inoculated with an aqueous spore suspension of *Pyrenophora teres* and incubated at 100% rel. atmospheric humidity for 16 hours in a climatic chamber. Cultivation of the infected plants was then continued in a greenhouse at 25° C. and 80% rel. atmospheric humidity.

About 1 week after inoculation the attack was evaluated and the degree of attack assessed in % of attacked leaf area in comparison with untreated, 100% infected controls.

With 250 mg of active compound/l of spray liquor the following substances show a complete suppression of attack:
Compounds from Examples 11 and 20

Example 4

*Erysiphe graminis*

Barley plants were heavily inoculated in the 3-leaf stage with conidia of powdery mildew of barley (*Erysiphe graminis* f. sp. *hordei*) and placed in a greenhouse at 20° C. and a relative atmospheric humidity of 90–95%. 24 hours after inoculation the plants were uniformly wetted with the compounds shown below at the active compound concentrations indicated. After an incubation time of 10 days, the plants were examined for attack with powdery mildew of barley. The degree of attack was expressed in % of attacked leaf area in comparison with untreated, 100% infected control plants.

With 250 mg of active compound/l of spray liquor the following substances show a complete suppression of attack:
Compounds from Examples 10 and 23.

Example 5

*Leptosphaeria nodorum*

Wheat plants of the variety "Jubilar" were treated in the 2-leaf stage until dripping wet with aqueous suspensions of the claimed compounds. After drying of the spray coating the plants were inoculated with an aqueous pycnospore suspension of *Leptosphaeria nodorum* and incubated in a climatic chamber at 100% rel. atmospheric humidity for several hours. Cultivation of the plants was continued in a greenhouse at about 90% rel. atmospheric humidity until expression of symptoms.

About 1 week after inoculation the degree of attack was assessed in % of attacked leaf area in comparison with untreated, 100% infected control plants.

With 250 mg of active compound/l of spray liquor the following substances show a complete suppression of attack:
Compounds from Examples 10 and 20

Example 6

*Botrytis cinerea*

About 14-day-old field beans of the varieties "Herz Freya" or "Frank's Ackerperle" were treated with aqueous suspensions of the claimed compounds until dripping wet. After drying of the spray coating the plants were inoculated with a spore suspension (1.5 million spores/ml) of *Botrytis cinerea*. Cultivation of the plants was continued in a climatic chamber at 20°–22° C. and about 99% rel. atmospheric humidity. Infection of the plants manifests itself in the formation of black spots on leaves and stalks. The evaluation of the tests was carried out about 1 week after inoculation. The degree of attack of the plants was assessed in percentage terms to untreated, 100% infected control plants.

With 250 mg of active compound/l of spray liquor the following compounds show a complete suppression of attack:

Compounds from Examples 10, 18, 11, 20 and 21

Example 7

Bean plants (*Phaseolus v.*) heavily attacked by two-spotted spider mites (*Tetranychus urticae*, full population) were sprayed with the aqueous dilution of a wettable powder concentrate which contained 250 ppm of the respective active compound.

The mortality of the mite was checked after 7 days. 100% destruction was achieved using the compounds as in Examples 15 and 10.

Example 8

Field beans (*Vicia faba*) heavily infested with black bean aphid (*Aphis fabae*) are sprayed with aqueous dilutions of wettable powder concentrates of 250 ppm active compound content up to the stage of the start of dripping off. The mortality of the aphids is determined after 3 days. A 100% destruction can be obtained using compounds as in Examples 20, 10 and the hydrochloride of 10.

Example 9

Bean plants heavily infested with greenhouse whiteflies (*Trialeurodes vaporariorum*) were sprayed with aqueous suspensions of wettable powder concentrates (250 ppm active compound content) until dripping off began. After placing the plants in the greenhouse, microscopic checking was carried out after 14 days with the result in each case of 100% mortality with the preparations containing the active compounds of Examples 20 and 10.

Example 10

L₃ larvae of the beetle species *Diabrotica undecimpunctate* were placed on filter paper discs which were saturated with 2 ml each of an aqueous dilution of a wettable powder concentrate which contained 250 ppm of active compound and stored in closed Petri dishes at room temperature (23° C.) for 3 days. The mortality of the larvae was then checked.

100% destruction was achieved with the compounds as in Examples 20, 11, 10 and the hydrochloride of 10.

Example 11

24-Hour-old imagines of the housefly (*Musca domestics*) were placed in glass Petri dishes. The bottom and cover had each been coated with 2 ml of an aqueous dilution of a wettable powder concentrate which contained 250 ppm of active compound. By drying in the air it was present as a coating on the glass surfaces.

3 hours after putting in the animals and closing the dishes the mortality was checked.

A 100% destruction was achieved using the compound from Example 15.

We claim:
1. A compound of the formula I

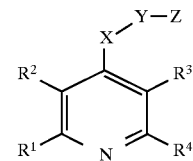

or its salts
in which
(1) $R^1$, $R^2$, $R^3$ and $R^4$ are identical or different radicals from the series
$(C_1-C_4)$-alkyl,
$(C_2-C_4)$-alkenyl,
$(C_1-C_4)$-alkoxy
$(C_2-C_4)$-alkenyloxy,
halo-$(C_1-C_4)$-alkyl,
halo-$(C_2-C_4)$-alkenyl,
halo-$(C_1-C_4)$-alkoxy,
halo-$(C_2-C_4)$-alkenyloxy,
R—O—CH$_2$—,
halo-$(C_1-C_4)$-alkoxymethyl,
halo-$(C_2-C_4)$-alkenyloxymethyl,
$(C_1-C_4)$-alkylthio,
$(C_2-C_4)$-alkenylthio,
$(C_1-C_4)$-alkylsulfinyl,
$(C_2-C_4)$-alkenylsulfinyl
$(C_1-C_4)$-alkylsulfonyl,
$(C_2-C_4)$-alkenylsulfonyl,
aryl,
substituted amino,
cyano,
halogen and
hydrogen;
    R is $(C_1-C_{10})$-alkyl,
       $(C_2-C_{10})$-alkenyl
       $(C_2-C_{10})$-alkynyl,
       $(C_3-C_8)$-cycloalkyl or
       aralkyl;
    aryl is phenyl or
       substituted phenyl
    aralkyl is aryl-$(C_1-C_4)$-alkyl;
(2) X is O, NH or NR, R being defined as above under (1);
(3) Y is a bond or a bivalent hydrocarbon radical having 1 to 6 carbon atoms, in which a methylene group can be replaced by an oxygen atom, and which is optionally substituted by one or more, identical or different radicals from the series
$(C_1-C_7)$-alkyl
$(C_2-C_4)$-alkenyl,
$(C_3-C_4)$-alkynyl,
halo-$(C_1-C_4)$-alkyl or
halogen; and
(4) Z is $(C_3-C_8)$-cycloalkyl or $(C_5-C_8)$-cycloalkenyl, which are both substituted by one or more identical or different radicals from the series
$(C_1-C_4)$-alkyl
$(C_2-C_4)$ alkenyl,
$(C_1-C_4)$-alkoxy,
$(C_1-C_4)$-alkanoyloxy,
$(C_2-C_4)$-alkenyloxy,
$(C_2-C_4)$-acyl,
$(C_1-C_4)$-alkoxycarbonyl,
$(C_2-C_4)$-alkenyloxycarbonyl,
halo-$(C_1-C_4)$-alkyl, halo-($C_2$–$C_4$)-alkenyl,
halo-($C_1$–$C_4$)-alkoxy,
halo-($C_2$–$C_4$)-alkenyloxy,
halo-($C_2$–$C_4$)-acyl,
halo-($C_1$–$C_4$)-alkoxycarbonyl,
halo-($C_2$–$C_4$)-alkenyloxycarbonyl,
halogen and
hydroxyl
in which at least one of said substituents is cis with respect to Y.

2. A compound of the formula 1 as claimed in claim 1, in which
(1) $R^1$, $R^2$, $R^3$ and $R^4$ are identical or different radicals from the series
($C_1$–$C_4$)-alkyl,
($C_2$–$C_4$)-alkenyl,
($C_1$–$C_4$)-alkoxy
($C_2$–$C_4$)-alkenyloxy,
halo-($C_1$–$C_4$)-alkyl,
halo-($C_2$–$C_4$)-alkenyl,
halo-($C_1$–$C_4$)-alkoxy,
halo-($C_2$–$C_4$)-alkenyloxy,
R—O—$CH_2$—,
halo-($C_1$–$C_4$)-alkoxymethyl,
halo-($C_2$–$C_4$)-alkenyloxymethyl,
cyano,
halogen and
hydrogen;
R is as defined in claim 1;
(2) X is O, or NH;
(3) Y is as defined in claim 1; and
(4) Z is ($C_3$–$C_8$)-cycloalkyl or ($C_5$–$C_8$)-cycloalkenyl, which are both substituted as defined in claim 1.

3. A compound of the formula 1 as claimed in claim 1 or its salts, in which
(1) $R^1$, $R^2$, $R^3$ and $R^4$ are the same or different radicals from the series
($C_1$–$C_4$)-alkyl,
($C_2$–$C_4$)-alkenyl,
($C_1$–$C_4$)-alkoxy
($C_2$–$C_4$)-alkenyloxy,
halo-($C_1$–$C_4$)-alkyl,
halo-($C_2$–$C_4$)-alkenyl,
halo-($C_1$–$C_4$)-alkoxy,
halo-($C_2$–$C_4$)-alkenyloxy,
R—O—$CH_2$—,
halo-($C_1$–$C_4$)-alkoxymethyl,
halo-($C_2$–$C_4$)-alkenyloxymethyl,
cyano,
halogen and
hydrogen;
R is as defined in claim 1;
(2) X is O or NH;
(3) Y is a bond or a bivalent hydrocarbon radical having 1 to 6 carbon atoms, in which a methylene group can be replaced by an oxygen atom, and which is optionally substituted by one or more, identical or different radicals from the series
($C_1$–$C_4$)-alkyl,
branched ($C_3$–$C_5$)-alkyl,
halo-($C_1$–$C_3$)-alkyl or
halogen; and
(4) Z is ($C_3$–$C_6$)-cycloalkyl, which is substituted as defined in claim 1.

4. A compound of the formula 1 as claimed in claim 1, in which Z is substituted cycloalkyl or cycloalkylene and the substituent is cis with respect to Y.

5. A compound of the formula 1 as claimed in claim 4, in which Z is cyclohexyl substituted once in the 4-position.

6. A composition, containing at least one compound as claimed in claim 1 and at least one formulating agent.

7. A fungicidal composition as claimed in claim 6, containing a fungicidally active amount of at least one compound as claimed in claim 1 together with the additives or auxiliaries customary for this application.

8. An insecticidal, acaricidal or nematicidal composition as claimed in claim 6, containing an active amount of at least one compound as claimed in claim 1 together with the additives or auxiliaries customary for these applications.

9. A plant protection composition, containing a fungicidally, insecticidally, acaricidally or nematicidally active amount of at least one compound as claimed in claim 1 and at least one further active compound, selected from the group consisting of fungicides, insecticides, baits, sterilants, acaricides, nematicides and herbicides series together with the auxiliaries and additives customary for this application.

10. A composition for use in wood preservation or as a preservative in sealing compositions, in painting colors, in cooling lubricants for metal processing or in drilling and cutting oils, containing an active amount of at least one compound as claimed in claim 1 together with the auxiliaries and additives customary for these applications.

11. A veterinary pharmaceutical for the control of endo- or ectoparasites containing an active amount for this application of a compound as claimed in claim 1 and a physiologically acceptable carrier.

12. A process for controlling phytopathogenic fungi, which comprises applying a fungicidally active amount of a compound as claimed in claim 1 or of a composition as claimed in claim 6 to these or the plants, surfaces or substrates attacked by them or to seeds.

13. A process for controlling harmful insects, Acarina and nematodes, in which an active amount of a compound as claimed in claim 1 or of a composition as claimed in claim 6 is applied to these or the plants, surfaces or substrates attacked by them.

14. A process for combating ectoparasites, which comprises addition of an active amount for this application of a compound as claimed in claim 1.

15. A seed, treated or coated with an active amount of a compound as claimed in claim 1 or a composition as claimed in claim 6.

* * * * *